United States Patent [19]
Post et al.

[11] Patent Number: 5,492,531
[45] Date of Patent: Feb. 20, 1996

[54] INFUSER APPARATUS FOR THE GASTRIC CAVITY

[75] Inventors: Gregory Post, East Amherst; Matthew Alesse, Amherst; Edwin T. Bean, Jr., Orchard Park, all of N.Y.

[73] Assignee: Ethox Corporation, Buffalo, N.Y.

[21] Appl. No.: 342,632

[22] Filed: Nov. 21, 1994

Related U.S. Application Data

[63] Continuation of Ser. No. 118,505, Sep. 8, 1993, abandoned.

[51] Int. Cl.$^6$ ................................................ A61M 37/00
[52] U.S. Cl. ........................ 604/82; 604/207; 604/905; 604/411; 604/403; 604/415
[58] Field of Search .................................. 604/82, 85, 131, 604/132, 257, 262, 403, 408, 410, 411, 412, 414, 415, 191, 185, 207, 241, 905; 222/94, 95, 98, 99, 101, 102, 103, 104, 213, 92; 128/767, 770

[56] References Cited

U.S. PATENT DOCUMENTS

| | | | |
|---|---|---|---|
| 1,959,896 | 5/1934 | Beebe | 604/207 |
| 3,677,248 | 7/1972 | McPhee . | |
| 3,990,447 | 11/1976 | Vega . | |
| 4,301,811 | 11/1981 | Layton . | |
| 4,306,976 | 12/1981 | Bazatto | 210/646 |
| 4,335,717 | 6/1982 | Bujan et al. . | |
| 4,336,802 | 6/1982 | Stone et al. | 604/905 X |
| 4,453,929 | 6/1984 | Silverman et al. . | |
| 4,525,156 | 6/1985 | Benusa et al. . | |
| 4,547,194 | 10/1985 | Moorehead | 604/283 |
| 4,607,868 | 8/1986 | Harvey et al. | 285/332 |
| 4,639,251 | 1/1987 | Kirkland | 604/262 |
| 4,664,293 | 5/1987 | Sheppard | 222/99 |
| 4,857,056 | 8/1989 | Talonn | 604/135 |
| 4,874,363 | 10/1989 | Abell | 604/28 |
| 4,946,445 | 8/1990 | Lynn | 604/192 |
| 5,188,628 | 2/1993 | Rani et al. | 604/411 |
| 5,211,626 | 5/1993 | Frank et al. | 604/65 |
| 5,251,873 | 10/1993 | Atkinson et al. | 251/149.1 |
| 5,289,858 | 3/1994 | Grabenkort | 141/97 |
| 5,300,060 | 4/1994 | Nelson | 604/410 |
| 5,308,347 | 5/1994 | Sunago et al. | 604/403 |
| 5,322,193 | 6/1994 | Sunderland | 222/99 |
| 5,391,150 | 2/1995 | Richmond | 604/111 |
| B14,340,052 | 7/1985 | Dennehey et al. | 604/283 |

Primary Examiner—C. Fred Rosenbaum
Assistant Examiner—V. Alexander
Attorney, Agent, or Firm—Hodgson, Russ, Andrews, Woods & Goodyear

[57] ABSTRACT

A stomach lavage apparatus for the introduction of a highly absorbent antidote solution, such as activated charcoal, into the gastric cavity for the purpose of absorbing or otherwise counteracting a digested poison present therein, is described. The lavage apparatus is a completely closed system so that the antidote solution is never exposed to the atmosphere and there is no risk of spilling the antidote solution. The present invention thus comprises a flexible container for the antidote solution, the container being connectable to a lavage conduit leading into the gastric cavity by threading the container into a fitting provided with an internal spike. This causes the spike to puncture a rupturable seal provided in an exit port of the container, and the container is then squeezed to express the antidote solution therefrom and into the lavage conduit for introduction into the gastric cavity. The fitting is preferably provided with another branch for connecting to a second container holding a flushing solution, such as water and the like.

10 Claims, 3 Drawing Sheets

INFUSER APPARATUS FOR THE GASTRIC CAVITY

This is a continuation of application Ser. No. 8/118,505 file on Sep. 8, 1993 now abandoned.

BACKGROUND OF THE INVENTION

1. Field of the Invention

This invention relates to a medical lavage apparatus that is useful for the introduction of an antidote solution into a patient's gastric cavity. More particularly, the present invention relates to a stomach lavage apparatus for the introduction of a highly absorbent activated carbon or charcoal solution into the gastric cavity for the purpose of absorbing ingested poisons. Frequently in drug overdose cases or in situations when a person has swallowed a highly toxic substance, it is undesirable to eliminate the poisonous substance through vomiting. Instead, it is preferred to counteract the effects of the poison in situ. Activated charcoal, due to its large surface area per unit volume, is a preferred antidote for this purpose.

2. Prior Art

U.S. Pat. No. 4,453,929 to Silverman et al. describes a flexible package containing a predetermined quantity of dry, finely divided activated charcoal. In use, a pharmaceutically acceptable liquid is filled into the package to bring the charcoal into solution and the package is then connected to a lavage tube for expressing the contents into the patient's gastric cavity. A problem with this device is that in drug overdose situations and the like, it is imperative that the poison in the stomach be neutralized as quickly as possible, and valuable time may be lost in preparing the charcoal solution.

U.S. Pat. No. 4,525,156 to Benusa describes a method for stomach lavage using a flexible reservoir bag intended to hold a diluent such a ice, water, saline solution, or other like medicinal solutions. This bag is connected to a double T-fitting for introducing the diluent into the gastric cavity. Another branch of the fitting provides for connection to a syringe that in use holds a poison antidote, such as activated charcoal. The antidote is flushed into the gastric cavity by the medicinal solution which together serve to neutralize the poison therein.

The drawback with this method is that activated charcoal as a poison antidote is very prone to soiling its surroundings including clothing, equipment and the like. This problem is particularly acute in a hospital environment where white garb is customarily worn and the surroundings are required to be sterilized. Contact with activated charcoal can easily ruin a clothing outfit or stain the surrounding hospital equipment. It is therefore, highly desirable to provide the antidote solution in a closed system that negates the possibility of spilling the antidote. In Benusa, it is necessary for the syringe to be periodically discounted from the double T-fitting for the purpose of refilling the syringe with the activated charcoal solution. Furthermore, even if the syringe is of a size to hold a complete dosage sufficient to neutralize an ingested quantity of poison, the syringe must be initially filled from a reservoir of activated charcoal. This filling step presents an opportunity for spilling the charcoal and thereby staining clothing and the like.

The Silverman et al. patent refers to the problem of some prepackaged solutions of activated charcoal having a short life when mixed with water or other pharmaceutically acceptable liquids. The problem is not that the charcoal loses its highly absorbent characteristics, but rather that after being stored for a period of time, the charcoal will have precipitated out of suspension and formed into clumps on the bottom of the container. At such time as the charcoal is needed for medicinal purposes, the container is intended to be turned upside down and the solution squeezed or otherwise expressed from a discharge port in the container. However, the precipitated activated charcoal remains clumped to the upwardly turned bottom of the container and not in a fully suspended state.

In the present invention, the antidote solution comprising prepackaged activated charcoal is provided with a basic suspending vehicle that prevents the charcoal from precipitating out of solution. Such a charcoal solution is commercially available, for example from Paddock Laboratories, Inc., Minneapolis, Minn. as Antidose™ with Sorbitol. This antidote solution can be stored for an extended period of time without the charcoal precipitating out of suspension and while retaining its highly absorbent characteristics.

SUMMARY OF THE INVENTION

The present invention provides a stomach lavage apparatus that is useful for introducing an antidote solution, such as a solution of activated charcoal and the like, into a patient's gastric cavity for the purpose of absorbing or otherwise counteracting a digested poison present therein. The lavage apparatus is a completely closed system so that during the stomach lavage procedure the antidote solution is never exposed to the atmosphere and there is no risk of spilling the antidote. The present invention thus comprises a flexible container holding a prepackaged antidote solution, such as an activated charcoal solution. The antidote container is connectable to a lavage conduit leading into the gastric cavity by threading the container into a fitting provided with an internal spike. This causes the spike to puncture a rupturable seal provided in the exit port of the container, and the container is then squeezed to express the antidote solution into the lavage conduit for introduction into the gastric cavity. The fitting is preferably provided with a separate branch for connecting to a second container holding a flushing solution, such as water and the like.

The container holding the antidote solution is preferably a flexible tube that is squeezed at the distal end spaced from the exit port to express the antidote solution therefrom. In some medical situations, the entire volume of the antidote solution is not needed all at once, and it is desirable to be able to prevent the container from unfolding at such time as the squeezing force is removed. The present invention provides an expressing key that fits over the distal end of the antidote tube, and the key is turned down onto the tube to express the contents therefrom. A locking means provided on the key serves to engage the tube for locking the tube in its partially expressed condition. This prevents the tube from unfolding after a portion of the antidote solution has been expressed therefrom.

BRIEF DESCRIPTION OF THE DRAWINGS

The above and other features and advantages of the present invention will become increasingly apparent to one of ordinary skill in the art by reference to the following detailed description of the preferred embodiments taken in conjunction with the accompanying drawings, in which.

DETAILED DESCRIPTION OF THE INVENTION

Figure 1:
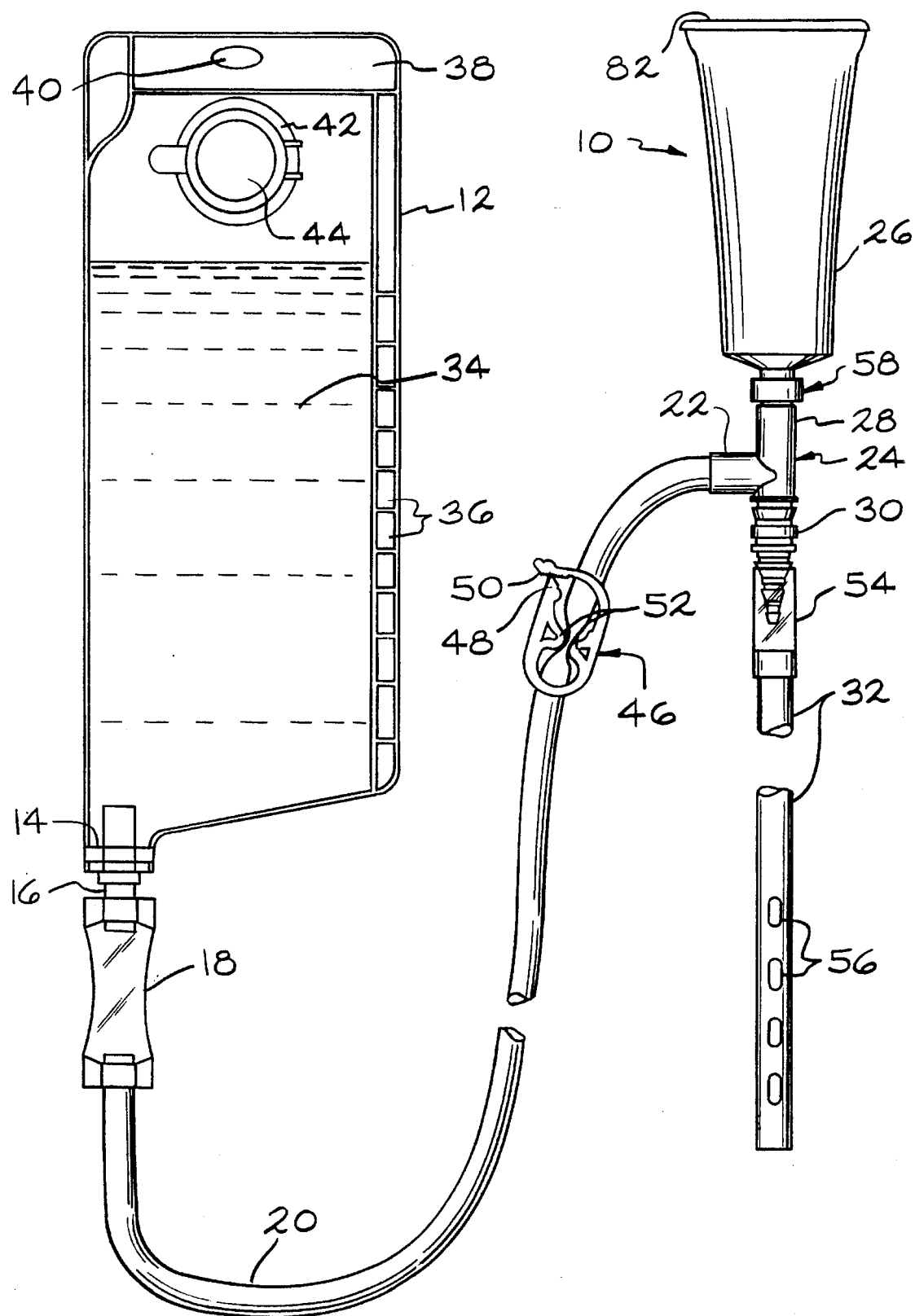
FIG. 1 is a schematic view of the stomach lavage system 10 of the present invention.

Referring now to the drawings, FIG. 1 is a schematic view showing the gastric cavity lavage system 10 of the present invention comprising a flexible liquid reservoir container, such as fluid bag 12 having a discharge port 14 fitted with a one-way check valve 16 leading to a flexible drip chamber 18. Drip chamber 18 is connected by a flushing conduit 20 to a first or middle inlet branch 22 of a T-connector 24. A tube shaped container 26 is filled with an antidote solution, such as an activated charcoal solution (not shown), and is connected to a second inlet branch 28 of connector 24. Connector 24 further comprises an outlet branch 30 provided with a lavage conduit 32.

Liquid reservoir bag 12 is of a commercially available type and preferably holds between about 2 to 4 liters of a liquid 34 used to flush the lavage system, as will be described in detail later. Bag 12 comprises opposed sheets of flexible material, preferably made of a clear plastic material such as a polyvinyl chloride (PVC) film of between about 4 to 8 mils thickness, that are heat sealed or otherwise joined along their common peripheries. A plurality of graduated scale marks 36 having embossed numerical indices (not shown) provided thereon extend along a lateral edge of bag 12 and serve as a liquid level indicator. An upper end of bag 12 forms a tab 38 having an opening or aperture 40 that receives a mounting hook (not shown) to hang bag 12 in an inverted position, as shown. This enables the liquid 34 contained therein to drain through discharge port 14. A fill port 42 having a hinged closable flap 44 is provided on one of the flexible sheets comprising bag 12, adjacent to and directly below aperture 40. The liquid 34 can comprise ice, water, and other medically acceptable solutions.

The discharge port 14 provided at the lower end of bag 12 has the one-way check valve 16, which allows the liquid 34 to flow from bag 12 and into the drip chamber 18, but prevents back flow into bag 12. Drip chamber 18 is a flexible member, preferably made of a clear plastic material such as polyvinyl chloride, having both of its upper and lower ends joined in a heat-sealed manner. The middle section of chamber 18 has a tubular shape that is squeezed to draw the liquid 34 from bag 12 and into chamber 18 through valve 16 and to then force the drawn-off liquid 34 into the flushing conduit 20 leading to T-connector 24.

Conduit 20 is made of a flexible tubular plastic material, such as polyvinyl chloride, and connects to the first inlet branch 22 of T-connector 24 in a liquid tight manner. An adjustable hand clamp 46 is positioned on conduit 20 and serves to constrict the conduit 20 and thereby regulate the flow therethrough and into connector 24. As shown in FIG. 1, clamp 46 is a unitary member having a generally D-shaped configuration provided by a first leg having a pawl 48 that is in a releasable locking engagement with ratchet teeth 50 provided on a second leg of clamp 46. The first and second legs of clamp 46 are further each provided with opposed, inwardly extending tabs 52 that serve to pinch conduit 20 and thereby constrict the fluid flow therethrough when pawl 48 is engaged with the ratchet teeth 50.

As shown in FIG. 1, the outlet branch 30 of T-connector 24 comprises a series of concentric frusto-conically shaped sections having incrementally decreasing outlet diameters connected by intermediate cylindrical sections. The frusto-conically shaped sections thereby provide for mounting a variety of different diameter sized gastric conduits, such as conduit 32. This is done by cutting the outlet branch 30 of connector 24 at that cylindrical section which is downstream from the one frustoconical section that will fit snugly into the inside diameter of the cylindrical fitting 54 sealed over the proximal end of gastric conduit 32. The distal end of gastric conduit 32 is open and the distal portion of gastric conduit 32 is provided with a plurality of oval shaped openings 56 extending therealong to provide for rapid discharge from conduit 32 of the antidote solution contained in tube 26 when conduit 32 is fed into the gastric cavity, and the antidote solution is expressed from tube 26, as will be explained in detail presently.

Figure 2:
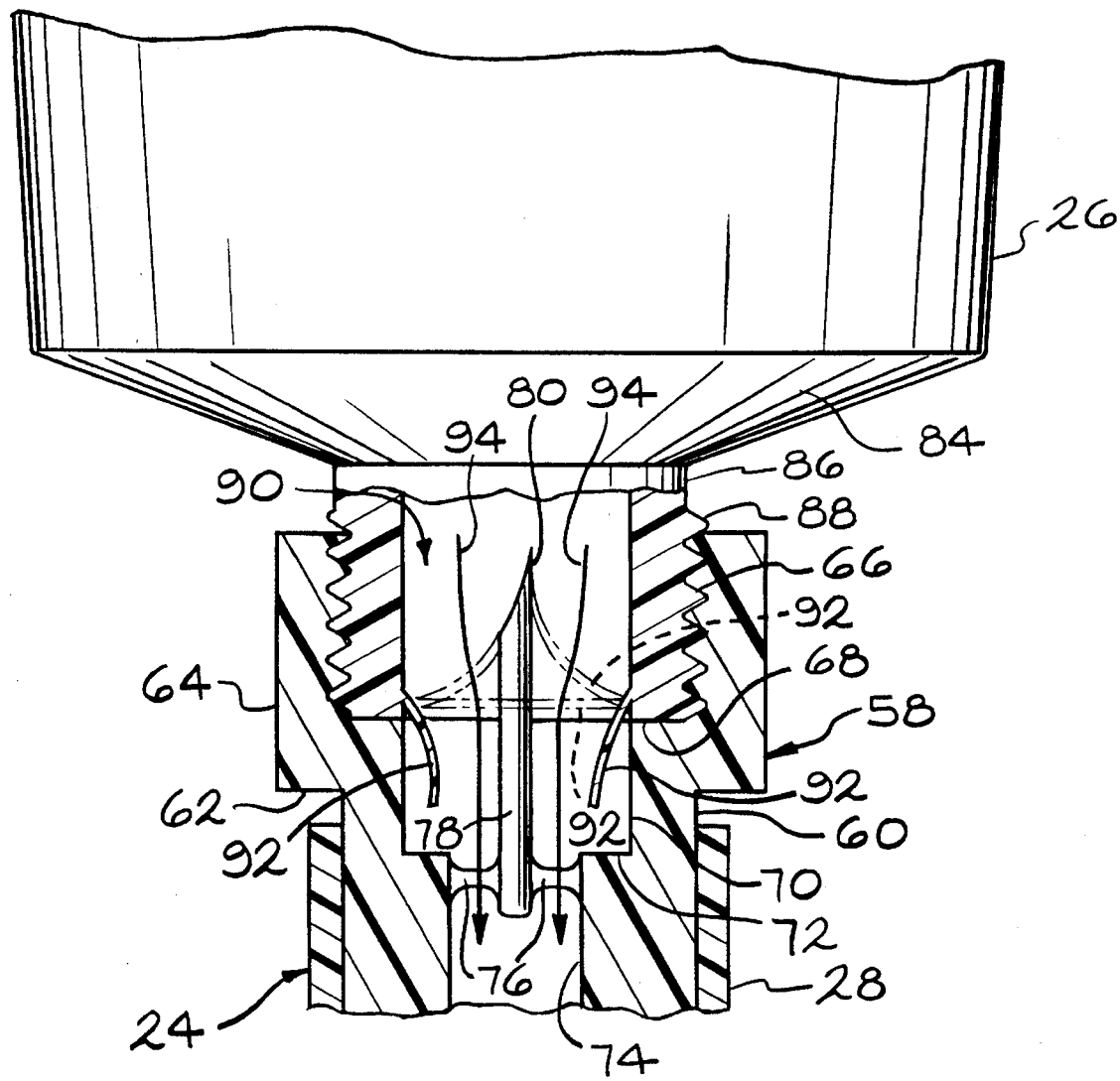
FIG. 2 is an expanded view, partly in cross-section, of the antidote solution tube 26 shown in FIG. 1, and threadedly secured to a T-shaped connector 24 having an internal piercing spike 78.

As shown in expanded cross-section in FIG. 2, the second inlet branch 28 of connector 24 is provided with a circular cross-sectional adaptor 58 having a first portion 60 with an outer circumference fitted inside the inlet branch 28. The first portion 60 of adaptor 58 extends to an outer step 62 that forms into a second portion 64 having a diameter that is larger than that of the first portion 60. Spaced radially inwardly of the second portion 64 is an inner threaded section 66 extending to a first internal step 68 that forms into an inner intermediate section 70 that in turn extends to a second internal step 72 forming into an inner downstream section 74 having a diameter less than that of the intermediate section 70. The inner downstream section 74 is provided with a plurality of inwardly extending radial arms 76 that bridge to a cylindrically shaped piercing member 78 provided with an inner through passage (not shown) and a beveled piercing point 80. Piercing point 80 is provided radially inwardly from the threaded section 66.

As further shown in FIG. 2, the inner threaded section 66 of adaptor 58 provides for mounting the tube 26 containing the antidote solution (not shown). Tube 26 comprises a generally circular cross-section formed by an annular side wall having a tab 82 (FIG. 1 and 3) provided at the distal end. Tab 82 is formed by heat-sealing opposed portions of the surrounding side wall together to join the opposed portions. The opposite end of tube 26 is provided with a neck 84 having a frusto-conical shape that tapers inwardly to a cylindrically shaped connector fitting 86 provided with threads 88 that serve to mate with the inner threaded section 66 of adaptor 58. Threaded connector 86 has a through passage 90 leading from the interior of tube 26 to a rupturable membrane 92 which closes the outer end of connector 86 (membrane 92 is shown in dashed lines in FIG. 2 in both the unruptured and ruptured positions).

As shown in FIG. 2, when tube 26 is threaded into engagement with adaptor 58, the piercing member 78 perforates membrane 92 to breach the sealed integrity of tube 26 so that upon the application of a squeezing force directed to tube 26, the antidote contents held therein, such as an activated charcoal solution, are expressed from the tube 26 and through the passage 90 provided in the threaded connector 86, as indicated by arrows 94. The force of the antidote solution expressing from tube 26 causes the ruptured membrane 92 to deflect outwardly and into the intermediate section 70 of adaptor 58 (deflected membrane 92 is shown in solid lines on FIG. 2), with the medicinal solution moving into the T-connector 24 to be flushed into the gastric conduit 32 and then into the patient's stomach by the liquid 34 flowing from bag 12.

Figure 3:
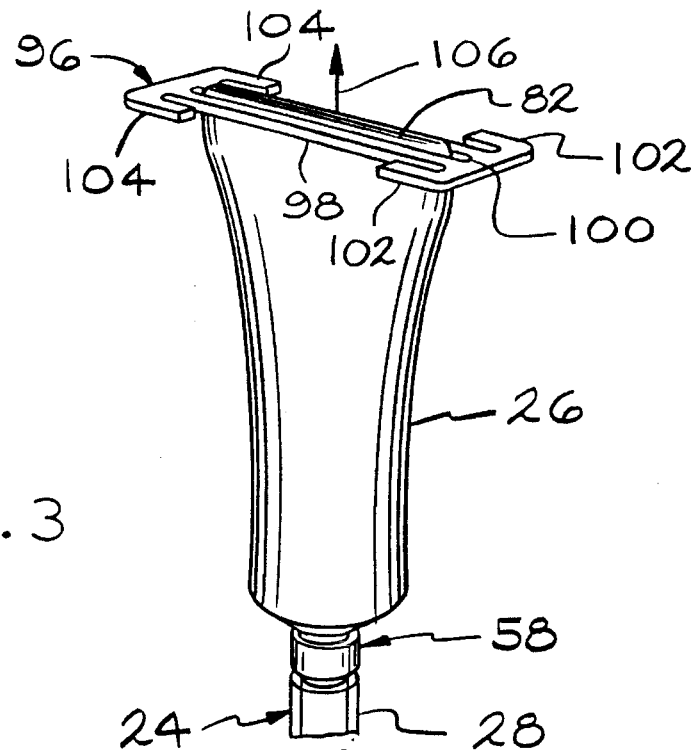
FIG. 3 is a perspective view showing an express key 96 mounted on the distal end of the antidote solution tube 26.
Figure 4:
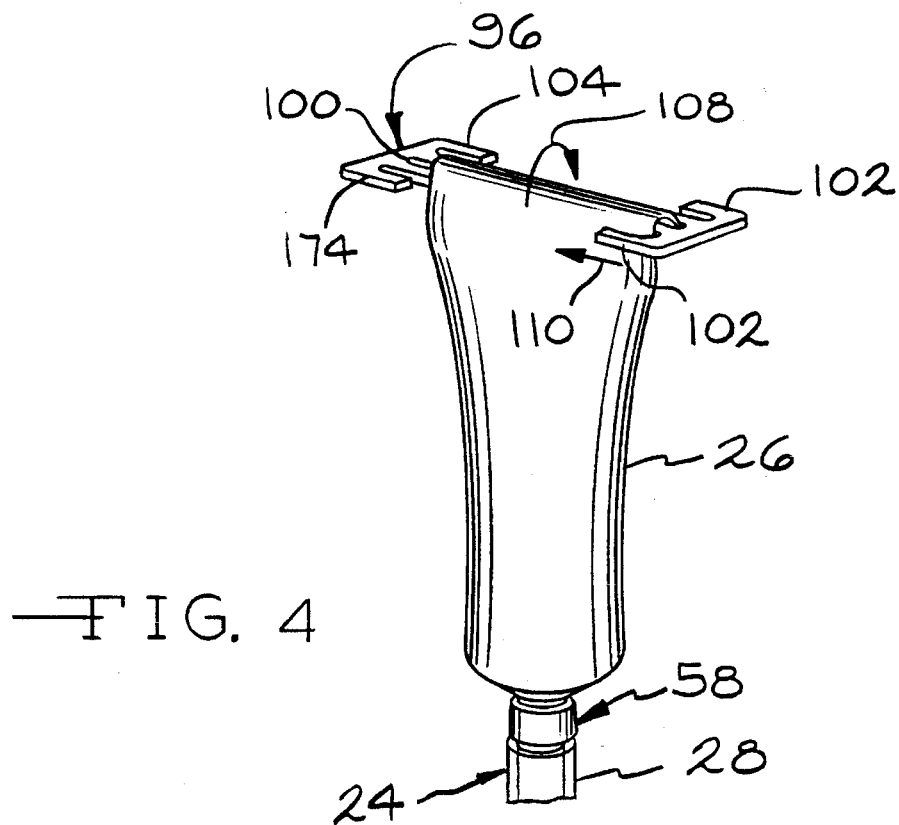
FIG. 4 is a perspective view of the express key 96 turned down upon the tube 26 shown in FIG. 4 to express the antidote solution therefrom.

As shown in FIGS. 3 and 4, the gastric lavage system 10 of the present invention also comprises an express key 96 that is positioned over and around the tab 82 provided at the distal end of tube 26 so that manipulation of key 96 in a turning motion serves to express the antidote solution from tube 26, as will be explained in detail presently. Key 96 is a planar member that can be made of plastic or metal and has a central portion 98 provided with an elongated oval shaped aperture 100 that is sized to fit over and around tab 82 at the distal end of tube 26. First and second pairs of ears 102 and 104 extend from the opposed ends of central portion 98, parallel with the longitudinal axis of key 96 and spaced radially outwardly from the central portion 98. In use, the tab 82 provided at the distal end of tube 26 is received inside the aperture 100 in key 96, as indicated by arrow 106 in FIG. 3. Key 96 is then held by one of its ends and turned down upon the tube 26, as indicated by arrow 108 in FIG. 4, to thereby express the antidote contents therefrom.

In those situations when the entire quantity of antidote solution contained in tube 26 is not required to be expressed therefrom and flushed into the patient's stomach, key 96 is moved in an axial direction, as indicated by arrow 110 in FIG. 4, so that one of the ears, in this case one of the ears 102, is caused to contact the outer surface of the side wall of tube 26 opposite the central portion 98 of key 96 to lock tube 26 in its partially expressed condition. It should be noted that the foregoing discussion related to the locking feature of key 96 applies to either of the first or second ears 102 and 104 provided at either of the opposed ends of the key 26, as can readily be appreciated by those of ordinary skill in the art.

In use, tube 26 provided with the antidote solution and express key 96 are preferably provided as a unit, and the gastric lavage system 10 of the present invention is assembled as schematically shown in FIG. 1. In that respect, the hinged flap 44 provided in bag 26 is opened and a medically acceptable liquid 34, such as water, ice and the like, is filled into bag 26 to a predetermined level as indicated by the graduated scale marks 36. Flap 44 is then closed to seal bag 26 and bag 26 is hung on a hook (not shown) moved through opening 40 in tab 38, The outlet branch 30 of the T-connector 24 is then cut to the appropriate size by severing that cylindrical section which is downstream from the one frusto-conically shaped section that fits snugly into the inside of fitting 54 provided at the proximal end of gastric tube 32 to provide a sealed conduit system therewith. The distal end of gastric conduit 32 having the oval shaped openings 56 is then moved into the patient's stomach. The patient preferably bites down on a bite block (not shown), as is known to those of ordinary skill in the art, and gastric tube 32 is moved through an opening in the bite block to position the gastric tube 32 in the patient's stomach.

A protector cap (not shown) threaded onto the outlet fitting 86 of tube 26 is removed, and the threads 88 provided on fitting 86 are mated with the threaded section 66 of adaptor 58 provided at the second inlet branch 28 of connector 24. As tube 26 is threaded into engagement with adaptor 58, the beveled piercing point 80 of piercing member 78 perforates the rupturable membrane 92 closing the outlet fitting 86 to access the antidote contents held therein. This way, the antidote solution inside tube 26 is completely segregated from the atmosphere which precludes any chance of spilling the solution. This is particularly important in those situations where sanitary conditions are required and the antidote solution comprises a highly solving solution such as an activated charcoal solution, where stained clothing is unacceptable, such as in a medical care environment.

Express key 96 is then positioned on tube 26 with the central aperture 100 in a surrounding relationship with respect to the tab 82 provided at the distal end of tube 26. Key 96 is then manipulated in a turning motion to fold the tube 26 down upon itself. This causes the antidote solution contained therein to express from tube 26, through the adaptor 58 and connector 24 and into the gastric conduit 32 for introduction into the patient's stomach.

The liquid 34 flows by gravity from bag 12, through the oneway check valve 16 into drip chamber 18. Drip chamber 18 is flexible and is squeezed to move the liquid 34 into the flushing conduit 20 where the liquid 34 flows by gravity into the first inlet branch 22 of T-connector 24 to serve as a flush for the antidote solution expressed from tube 26 and into connector 24. The flow of flushing liquid 34 through conduit 20 and into connector 24 is regulated by hand clamp 46 by adjusting the ratchet relationship between pawl 48 and the ratchet teeth 50, as is known to those of ordinary skill in the act. Should the medical provider operating the lavage system 10 of the present invention desire to increase the flow of flushing liquid 34 flowing through conduit 20 and into connector 24, an upwardly directed force is applied to the end of the second leg of clamp 46 having the ratchet teeth 50 to disengage the ratchet relationship between pawl 48 and teeth 50. The resilient material comprising clamp 46 then causes the extending tabs 52 comprising the opposed legs of clamp 46 Co move further apart and thereby provide for the increased fluid flow of flushing liquid 35 into connector 24 and then into gastric conduit 32. The flushing liquid 34 is prevented from back flowing into tube 26 by the antidote solution contained therein and the positive pressure being applied to the antidote solution by the folded tube 26.

It can readily be understood that the gastric lavage system 10 of the present invention can be used for its intended purpose without the problem of having the antidote solution contained in tube, such as activated charcoal, spilled onto the clothing of attendant medical staff and onto the surrounding equipment. Additionally, the present gastric lavage system 10 provides a completely enclosed system that is simple to operate, inexpensive to manufacture, lightweight in construction and that is readily and quickly assembled, easy to store, and disposable following use.

It is intended that the foregoing descriptions only be illustrative of the present invention and the present invention is intended to be limited only by the hereinafter appended claims.

We claim:

1. A lavage kit for introducing an antidote solution into a gastric cavity, which comprises:
   a) a flexible container means provided with the antidote solution and comprising a surrounding side wall extending from a sealed opening that is breachable for expression of the antidote solution therefrom, wherein the container means is provided with a first threaded means surrounding the sealed opening;
   b) conduit means having a first end provided with a second threaded means that is threadably engagable with the first threaded means of the container means, and a rupture means provided inside the second threaded means, the rupture means serving to rupture the sealed opening only after such time as the first threaded means is threadingly engaged with the second threaded means of the container means so that the antidote solution cannot inadvertently express from the container means to the atmosphere but is confined in the first end of the conduit means by the threaded engagement between the first and second threaded means and wherein the conduit means has a second end adapted to deliver the antidote solution to the gastric cavity;

c) expression means comprising a plate means having an elongated slot therein that receives the side wall comprising the container means in a surrounding relationship so that opposed sides of the expression means are provided proximate opposed portions of the side wall of the container means, wherein the expression means is manipulatable to fold the container means down upon itself and thereby move the opposed portions of the surrounding side wall comprising the container means into a proximate relationship with respect to each other to thereby provide for expression of the antidote solution through the sealed opening after the sealed opening has been breached by the rupture means; and d) a locking means provided on the expression means and manipulatable to contact a portion of the side wall of the container means, which contacted portion is opposite the expression means with the container means folded down upon itself to thereby lock the container means in its partially expressed condition.

2. The kit of claim 1 wherein the plate means is an elongated member having a longitudinal axis and the slot is aligned along the axis of the plate means.

3. The kit of claim 1 wherein the locking means comprises opposed tab means extending from at least the opposite corners of one end of the plate means and adjacent to an end of the slot, wherein the tab means each have a second longitudinal axis parallel and spaced from the longitudinal axis of the plate means with an open ended slot provided between a side of each tab and an adjacent side of the plate means such that the expression means is manipulatable to cause one of the tab means to contact the container means with a portion of the side wall comprising the container means turned down upon itself provided at an intermediate position between the secondary slot formed between the one tab means and an opposite portion of the plate means to thereby lock the container means in a partially expressed condition.

4. A totally enclosed stomach lavage system for introducing an antidote solution into a gastric cavity, comprising:

a) a container means containing the antidote solution and having a sealed opening that is breachable for expression of the antidote solution therefrom;

b) a first threaded means provided on the container means surrounding the sealed opening;

c) a connector means comprising a first inlet branch, a second inlet branch provided with a second threaded means, a rupture means provided inside the second inlet branch surrounded by the second threaded means, and an outlet branch wherein the sealed opening of the container means is rupturable by the rupture means only after such time as the first threaded means is threadingly engaged with the second threaded means so that the antidote solution cannot inadvertently express from the container means to the atmosphere but is confined in the second inlet of the connector means by the threaded engagement between the first and second threaded means;

d) a conduit means having a proximal end connected to the outlet branch of the connector means and a distal end insertable into the gastric cavity;

e) a flushing conduit means having a proximal end connected to the first branch of the connector means and a distal end connected to a reservoir means having a discharge port and provided with a flushing fluid;

f) an expression means positionable on the container means and manipulatable to express the antidote solution from the container means and into the connector means after the sealed opening has been breached by the rupture means and then from the connector means into the conduit means for introduction of the antidote solution into the gastric conduit means, and wherein the flushing fluid is movable from the liquid reservoir and into the first branch of the connector means to there meet the antidote solution present in the connector means, the flushing fluid serving to aid in moving the antidote solution into the conduit means; and g) a locking means provided on the expression means and manipulatable to lock the container means in its partially expressed condition and wherein the expression means is positionable in a surrounding relationship with respect to the side wall comprising the container means so that opposed sides of the expression means are provided proximate opposed portions of the side wall comprising the container means, and wherein the expression means is manipulatable to fold the container means down upon itself to move the opposed portions of the surrounding side wall comprising the container means into a proximate relationship with respect to each other and thereby provide for expression of the antidote solution therefrom at such time as the sealed opening is ruptured by the rupture means and wherein the expression means comprises a plate means having an elongated slot that is positionable in a surrounding relationship with respect to the side wall comprising the container means and wherein the locking means comprise opposed tab means extending from at least the opposite corners of one end of the plate means and adjacent to an end of the slot, wherein the tab means each have a second longitudinal axis spaced from and parallel to the longitudinal axis of the plate means with an open ended slot provided between a side of each tab and an adjacent side of the plate means such that the expression means is manipulatable to cause one of the tab means to contact the container means with a portion of the side wall comprising the container means turned down upon itself and received in one of the open ended slots to thereby lock the container means in a partially expressed condition.

5. A method for providing a closed stomach lavage, comprising the steps of:

(a) providing a flexible container means holding an antidote solution and having a sealed opening that is breachable for expression of the antidote solution therefrom;

(b) providing a connector means having at least two intersecting branches, one of the branches being provided with a first mating means that is connectable to a second mating means provided at the sealed opening to mate the container means with the connector means, and including the step of the mating the container means to the one branch of the connector means by joining the first and second mating means and wherein the one branch of the connector means is provided with a rupture means that breaches the sealed opening when the container means is mated to the connector means; and (c) expressing the antidote solution from the container means and through the connector means to a conduit means connected to the second branch of the connector means, the conduit means leading into the stomach of a patient.

6. The method of claim 5 wherein the connector means is a T-connector with a third branch connected to a flush liquid and including the step of flushing the antidote solution into the patient's stomach by expressing the flush liquid through the third branch and into the connector means while expressing the antidote solution from the container means.

7. The method of claim 5 wherein the container means comprises a surrounding side wall extending from the sealed opening to a joined portion comprising at least two portions of the side wall meeting along a common edge and wherein an expression means for the container means is provided and including the step of positioning the expression means in an engaged relationship with respect to the joined portion of the container means so that opposed sides of the expression means are provided proximate the side wall comprising the container means and then manipulating the expression means to fold the container means down upon itself by moving opposite portions of the surrounding side wall into a proximate relationship with respect to each other thereby expressing the antidote solution through the container opening breached by the rupture means.

8. The method of claim 5 wherein the expression means is provided with a locking means and including the step of enabling the locking means so that the locking means contacts a portion of the side wall of the container means, opposite the expression means with the container means folded down upon itself to thereby lock the container means in its partially expressed condition.

9. The method of claim 5 wherein the expression means comprises a plate means having an elongated slot therein and including the step of positioning the expression means on the container means with the joined portion of the container means received in the slot means of the plate means and then manipulating the plate means in a turning motion to fold the container means down upon itself with the container means winding around the plate means so that opposed portions of the surrounding side wall move into a proximate relationship with respect to each other thereby expressing the antidote solution through the container opening breached by the rupture means.

10. The method of claim 9 wherein the plate means of the expression means further includes opposed tab means extending from at least the opposite corners of one end of the plate means and adjacent to an end of the slot, wherein the tab means each have a second longitudinal axis spaced from and parallel to the longitudinal axis of the plate means with an open ended slot provided between a side of each tab and an adjacent side of the plate means and including the step of manipulating the expression means to cause one of the tab means to contact the container means with a portion of the side wall comprising the container means turned down upon itself and received in one of the open ended slots to thereby lock the container means in the partially expressed condition.

* * * * *